US008474455B2

(12) United States Patent
Soliman et al.

(10) Patent No.: US 8,474,455 B2
(45) Date of Patent: *Jul. 2, 2013

(54) SYSTEM AND METHOD FOR CIRCUIT COMPLIANCE COMPENSATED VOLUME ASSURED PRESSURE CONTROL IN A PATIENT RESPIRATORY VENTILATOR

(75) Inventors: Ihab S. Soliman, Laguna Niguel, CA (US); Steven Duquette, Laguna Niguel, CA (US)

(73) Assignee: CareFusion 207, Inc., San Diego, CA (US)

( * ) Notice: Subject to any disclaimer, the term of this patent is extended or adjusted under 35 U.S.C. 154(b) by 1161 days.

This patent is subject to a terminal disclaimer.

(21) Appl. No.: 11/328,523

(22) Filed: Jan. 10, 2006

(65) Prior Publication Data

US 2007/0157930 A1 Jul. 12, 2007

(51) Int. Cl.
*A61M 16/00* (2006.01)

(52) U.S. Cl.
USPC ............ 128/204.21; 128/200.24; 128/204.18; 128/204.22; 128/204.23; 128/204.25; 128/204.26

(58) Field of Classification Search
USPC ............. 128/200.24, 203.12, 203.13, 204.18, 128/204.21, 204.22, 204.23, 204.24, 204.25, 128/204.26; 702/1, 45, 50, 55, 127, 138; 700/90, 213, 231, 240, 244, 281, 282, 301, 700/305; 222/1, 3, 52, 55
See application file for complete search history.

(56) References Cited

U.S. PATENT DOCUMENTS

| | | | |
|---|---|---|---|
| 4,448,192 A * | 5/1984 | Stawitcke et al. ........ | 128/204.26 |
| 4,602,653 A | 7/1986 | Ruiz-Vela et al. | |
| 4,989,456 A | 2/1991 | Stupecky | |
| 5,038,621 A | 8/1991 | Stupecky | |
| 5,044,362 A * | 9/1991 | Younes ..................... | 128/204.21 |
| 5,107,830 A * | 4/1992 | Younes ..................... | 128/204.18 |
| 5,127,400 A | 7/1992 | DeVries et al. | |
| 5,178,151 A * | 1/1993 | Sackner ......................... | 600/485 |
| 5,197,895 A | 3/1993 | Stupecky | |
| 5,303,698 A * | 4/1994 | Tobia et al. .............. | 128/204.21 |
| 5,331,995 A * | 7/1994 | Westfall et al. .................... | 137/8 |
| 5,405,269 A | 4/1995 | Stupecky | |
| 5,429,123 A * | 7/1995 | Shaffer et al. ............ | 128/204.23 |
| 5,494,028 A * | 2/1996 | DeVries et al. .......... | 128/205.24 |
| 5,598,838 A * | 2/1997 | Servidio et al. .......... | 128/204.23 |
| 5,927,274 A * | 7/1999 | Servidio et al. .......... | 128/204.18 |
| 5,931,160 A * | 8/1999 | Gilmore et al. .......... | 128/204.21 |
| 6,015,388 A * | 1/2000 | Sackner et al. ............... | 600/529 |
| 6,305,374 B1 * | 10/2001 | Zdrojkowski et al. ... | 128/204.21 |
| D459,477 S | 6/2002 | Stocks et al. | |
| D461,234 S | 8/2002 | Hanna | |
| 6,435,182 B1 * | 8/2002 | Lutchen et al. .......... | 128/204.21 |

(Continued)

*Primary Examiner* — Annette Dixon

(74) *Attorney, Agent, or Firm* — McDermott Will & Emery LLP

(57) ABSTRACT

A system for circuit compliance compensated volume assurance pressure control in a patient respiratory ventilation circuit, having a patient circuit volume estimator for estimating a patient circuit compliance, a patient circuit volume estimator to estimate a circuit volume $VOL_{CKT\_EST}$ based on the patient circuit compliance, a patient volume observer, for estimating a patient volume $VOL_{TID\_EST}$ based on a measure delivered net volume $VOL_{NET}$ and the patient circuit compliance, a volume assurance controller for generating a circuit compliance volume compensation factor $VOL_{TID\_CTL}$ based on a preset assured volume $VOL_{ASS\_SET}$ and the estimated patient volume $VOL_{TID\_EST}$, and a decelerating inspiratory flow controller, operative to generate a decelerating inspiratory peak flow based on a preset inspiratory time $T_{INSP}$ and the volume compensation factor $VOL_{TID\_CTL}$.

56 Claims, 4 Drawing Sheets

U.S. PATENT DOCUMENTS

| | | | |
|---|---|---|---|
| 6,948,497 B2 * | 9/2005 | Zdrojkowski et al. | 128/204.18 |
| 6,968,842 B1 * | 11/2005 | Truschel et al. | 128/204.18 |
| 7,100,607 B2 * | 9/2006 | Zdrojkowski et al. | 128/204.18 |
| 2003/0097880 A1 | 5/2003 | Ciobanu et al. | |
| 2003/0106554 A1 | 6/2003 | de Silva et al. | |
| 2007/0089738 A1 * | 4/2007 | Soliman et al. | 128/202.22 |
| 2007/0101992 A1 * | 5/2007 | Soliman et al. | 128/204.21 |

* cited by examiner

SYSTEM AND METHOD FOR CIRCUIT COMPLIANCE COMPENSATED VOLUME ASSURED PRESSURE CONTROL IN A PATIENT RESPIRATORY VENTILATOR

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention relates in general to a patient respiratory ventilator and, more particularly, to a system and a method for circuit compliance compensated volume assured pressure control in a patient respiratory ventilator.

In order to accurately deliver at least a set assured volume to the patient during a pressure-control mode of ventilation, a ventilator must compensate for patient circuit compliance. This is particularly crucial for neonatal patients for whom the circuit compliance is often much larger than the lung compliance. Without adequate compensation of the patient circuit compliance, inaccurate volume and flow may be delivered to the patient. Included in the prior art are several approaches of patient circuit compliance. These prior art approaches have been designed and applied to currently available ventilators such as the AVEA® Comprehensive Ventilator, commercially available from Viasys Healthcare Inc., assignee of the subject disclosure.

Unfortunately, most of the approaches, while compensating for the patient circuit compliance, inevitably cause gas trapping and auto PEEP, which consequently impacts the ability of the patient to exhale the delivered tidal volume. Therefore, many ventilators of the prior art do not allow application of patient circuit compliance to neonatal patients due to the stringent volume precision requirement. The burden of providing accurate volume delivery is thus shifted to the clinician.

Currently, known volume assurance algorithms, such as may be used with the AVEA® Comprehensive Ventilator mentioned above as well as other prior art ventilators, are typically only suitable for pediatric and adult-sized patients. In such volume assurance algorithms, when a volume assurance is set in a pressure-controlled mode, the inspiratory flow controller command is the maximum of the pressure-control flow command and a decelerating flow command. Therefore, depending on the set inspiratory pressure, assured volume, airway resistance, lung compliance and circuit compliance, the breath delivery can result in a pressure-controlled breath, a volume controlled breath, or a hybrid of pressure and volume controlled breath.

By setting the volume assurance, a decelerating flow command profile for the current breath is generated by using an estimate of circuit volume from the previous breath, the set assured volume and the set inspiratory time. During inspiration, the decelerating flow command will be terminated if the system delivered volume, as measured by the inspiratory sensor, exceeds the set assured volume and the circuit volume that is computed during the breath. The breath is cycled to exhalation control when the set inspiratory time is reached and the system delivered volume exceeds the set assured volume & circuit volume computed during the breath.

Using a MATLAB®-based rapid prototyping HITL system, simulated applications of the above-mentioned algorithm to different patient sizes, including neonates, have been performed and certain deficiencies in the algorithm have been discovered. Firstly, during ventilation of a patient, the system may not achieve the desired volume delivery within the set inspiratory time. This is particularly a problem for neonate patients where the circuit to lung compliance ratio can be large. If the delivered system volume fails to reach the set assured and circuit volumes within the set inspiratory time, the inspiratory time is extended to allow time for volume delivery until the I:E ratio limit is eventually reached. In most cases, the system consecutively reaches the I:E ratio limit for up to 5 breaths before stabilization. Secondly, for cases where the circuit to lung compliance ratio is as high as 13:1 and a minimal set inspiratory time is set, volume delivery errors may occur if the decelerating flow command reaches the allowable maximum flow command.

This can be a problem when the airway resistance is high and additional flow is required to compensate for the circuit compliance. The I:E limit will be reached in these cases because the flow required to compensate for the circuit volume cannot be achieved. Thirdly, because net system delivery volume is not used, exhalation valve leaks during inspiration are not accounted for during volume delivery. This can significantly affect the accuracy of volume delivery. Fourthly, excess volume delivery due to flow control valve closing dynamics is not accounted for during volume delivery. Fortunately, this may not be as critical in the pressure-control mode with a set volume assurance since only a minimum volume is required.

BRIEF SUMMARY

Provided is a volume assurance algorithm that is based upon the currently-available approach as described above. However, the volume assurance algorithm as provided herein shifts from direct use of patient circuit volume for volume delivery to a servo control system approach for volume delivery. More specifically, instead of directly using the patient circuit volume in an open-loop system for volume delivery, the patient circuit volume is used to estimate the patient volume for feedback control. Based on measurements provided by sensors in the patient circuit, the patient delivered volume is estimated by a conceptual volume observer or virtual sensor.

When the patient circuit compliance is estimated and a machine delivered net volume that accounts for leaks and valve dynamics is measured, such values are used to estimate the patient delivered volume. The estimated patient delivered volume is then fed back via a feedback volume controller. The difference between the estimated patient delivered volume and the set assured volume is used to modulate the required system volume to be delivered. The feedback volume controller for modulating the delivered system volume is executed on a breath-by-breath basis in order to achieve the set assured volume.

At the beginning of every breath, the commanded system volume to be delivered is converted to a decelerating flow command profile based on the set inspiratory time. The decelerating flow command profile for the current breath compensates for volume delivery errors, exhalation valve leaks, flow control valve closing dynamics and changes in patient conditions. The final inspiratory flow controller command is the maximum of the pressure control flow command and the decelerating flow command when the volume assurance is set.

Thus, depending on the set inspiratory pressure, assured volume, airway resistance, lung compliance and circuit compliance, the breath delivery can result in a pressure controlled breath, a volume controlled breath, or a hybrid of pressure and volume controlled breath. When a patient wye ("Y") flow sensor is also used, a volume limit can be set up by the measurement thereof. Alternatively, the volume measured by the patient Y flow sensor can also be used as the feedback patient delivered volume for modulating the system delivered volume.

The volume assurance algorithm can be used in a method and a system for circuit compliance compensated volume assured pressure control in a patient respiratory ventilator. In the system for circuit compliance compensated volume assured pressure control, the system volume command is adjusted based on the error between the estimated patient delivered volume from the last breath and the set assured volume at the start of every new breath. The required decelerating flow command profile is then computed and updated into a volume assurance controller flow command based on the adjusted system volume command and a set inspiratory time for the breath.

An inspiratory flow controller command is set as the maximum of the pressure controller flow command and the volume assurance controller flow command. When the system delivered volume in the inspiratory phase exceeds the updated system volume command (which is equal to the sum of the set assured volume and a volume controller correction) and when the set inspiratory time is reached, the breath cycles to an exhalation phase.

After cycling to the exhalation phase, the estimate of patient circuit volume is updated using the circuit compliance estimate and the measured patient Y pressure when the net system flow passes zero. The estimate of patient volume for the current breath is also updated using the updated patient circuit volume and the measured net delivered system volume. These steps are repeated breath-by-breath for the duration of patient ventilation.

BRIEF DESCRIPTION OF THE DRAWINGS

These and other features and advantages of the various embodiments disclosed herein will be better understood with respect to the following description and drawings in which like numbers refer to like parts throughout and in which.

DETAILED DESCRIPTION

The system and method for circuit compliance compensated volume assured pressure control in a patient respiratory ventilator is based upon a similar theory of operation as disclosed in U.S. patent application Ser. No. 11/247,568 entitled "System and Method for Circuit Compliance Compensated Volume Control in a Patient Respiratory Ventilator", filed Oct. 11, 2005, and in U.S. patent application entitled "System and Method for Circuit Compliance Compensated Pressure Regulated Volume Control in a Patient Respiratory Ventilator" filed Nov. 9, 2005 assigned to the same assignee as the present invention, the disclosures of both applications being expressly incorporated herein by reference.

Figure 1:
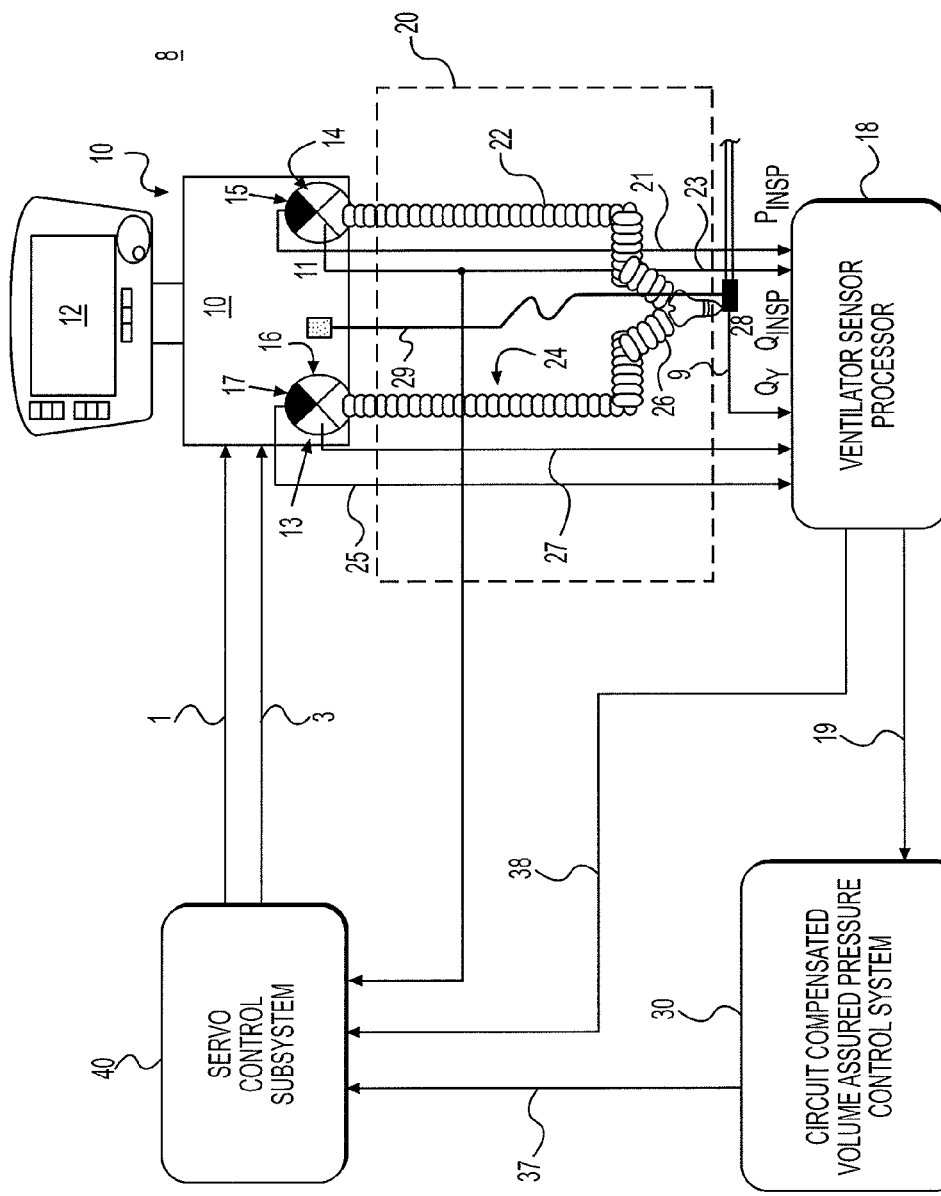
FIG. 1 illustrates a patient respiratory circuit employing a system for circuit compliance compensated volume assured pressure control.

FIG. 1 illustrates a patient respiratory circuit or a ventilation system that utilizes a system for circuit compliance compensated volume assured pressure control as provided herein. As shown, the ventilation system includes a circuit compliance compensated volume assured pressure control in a patient respiratory ventilator system 8, a patient ventilator 10, a patient circuit 20 for circulating the inspiratory gas and the expiratory gas between the ventilator 10 and a patient, the system for circuit compliance compensated volume assured pressure control 30, and a servo control subsystem 40 for controlling operations of the ventilator 10. The ventilator 10 has an inspiratory port 14 and an expiratory port 16 through which the inspiratory gas and the expiratory gas are supplied to and received from the patient through the patient circuit 20.

An inhalation flow control valve or orifice is typically installed at the inspiratory port 14 for controlling the inspiratory flow $Q_{INSP}$ 23, and an exhalation valve is preferably installed at the expiratory port for controlling the open/close conditions of the expiratory port 16. In this embodiment, inspiratory and expiratory flow sensors 11 and 13 are disposed adjacent to the inspiratory and expiratory ports 14 and 16 and are configured for measuring the inspiratory $Q_{INSP}$ 23 and expiratory flows $Q_{EXP}$ 27, respectively. In addition, an inspiratory pressure transducer 15 and an expiratory pressure transducer 17 may also be installed to measure the inspiratory and expiratory pressures $P_{INSP}$ 21 and $P_{EXP}$, respectively.

The patient circuit 20, such as includes a Y circuit 26, is used to connect the ventilator 10 to the patient so as to construct the respiratory circuit for circulating gas between the ventilator 10 and the patient. The Y circuit 20 26 includes an inspiratory limb 22 with one end connected to the inspiratory port 14 and an expiratory limb 24 with one end connected to the expiratory port 16 of the ventilator 10. The other ends of the inspiratory limb 22 and the expiratory limb 24 merge with each other at one end of a patient Y piece 26 of which an opposite end is applied to the patient Other accessories or component devices such as filters may also be installed in various locations of the Y circuit 20 26. For example, a flow sensor 28 is preferably installed at the patient piece to directly measure the patient flow $Q_y$ 9delivered to the patient. It will be appreciated that the inspiratory and expiratory flow sensors 11 and 13 may also be installed on the inspiratory limb 22 and the expiratory limb 24, respectively. Preferably, the measurable process variables, including the inspiratory flow $Q_{INSP}$ 23, the expiratory flow $Q_{Exp}$ 27, the inspiratory pressure $P_{INSP}$ 21, the expiratory pressure $P_{EXP}$, and positive end expiratory pressure PEEP 25 are measured according to a predetermined sampling rate. For example, in one embodiment, these process variables are sampled every 2 msec.

The ventilator 10 may further comprise a sensor processor 18 that is preferably operative to process the measured process variables or parameters, including $Q_{INSP}$ 23, $Q_{EXP}$ 27, $P_{INSP}$ 21, $P_{EXP}$ and other sensor readings such as $Q_y$ 9 and calculating or computing the desired variables such as the estimated patient pressure $P_y$ 38, estimated machine net volume $VOL_{NET}$ 63, the estimated patient tidal volume $VOL_{TID}$ 7, PEEP 25 and the measured patient volume $V_y$ and are sent via patient pressure data 19 for to the circuit compliance compensated volume assured pressure control system 30. The sensor processor 18 may be configured as an individual sensor in communication with the sensors 11, 13, 15, 17 and 28 and the circuit compliance compensated volume assured pressure control system 30, integrated into the ventilator 10, or incorporated into the system for circuit compliance compensated volume assured pressure control 30.

Preferably, the patient pressure $P_y$ 38 is defined as the expiratory pressure $P_{EXP}$ measured from the expiratory pressure transducer 17 during the inspiratory phase, and the average of the expiratory pressure $P_{EXP}$ and the inspiratory pressure $P_{INSP}$ 21 measured from the inspiratory pressure transducer 15 during the expiratory phase. That is, based on the following Equation (1), the sensor processor 18 is operative to compute and output the patient pressure $P_y$ to the circuit compliance compensated volume assured pressure control system 30.

$$P_Y = \begin{cases} P_{\text{EXP}}, & \text{during } I\text{-phase} \\ (P_{INSP} + P_{\text{EXP}})/2, & \text{during } E\text{-phase} \end{cases} \quad (1)$$

In addition to the patient pressure $P_y$, the sensor processor 18 is also operative to compute the machined delivered volume $VOL_{NET}$ 63 by integrating the net flow $Q_{NET}$ 77 defined as the flow difference between the inspiratory flow $Q_{INSP}$ 23 and the expiratory flow $Q_{EXP}$ 27.

Figure 2:
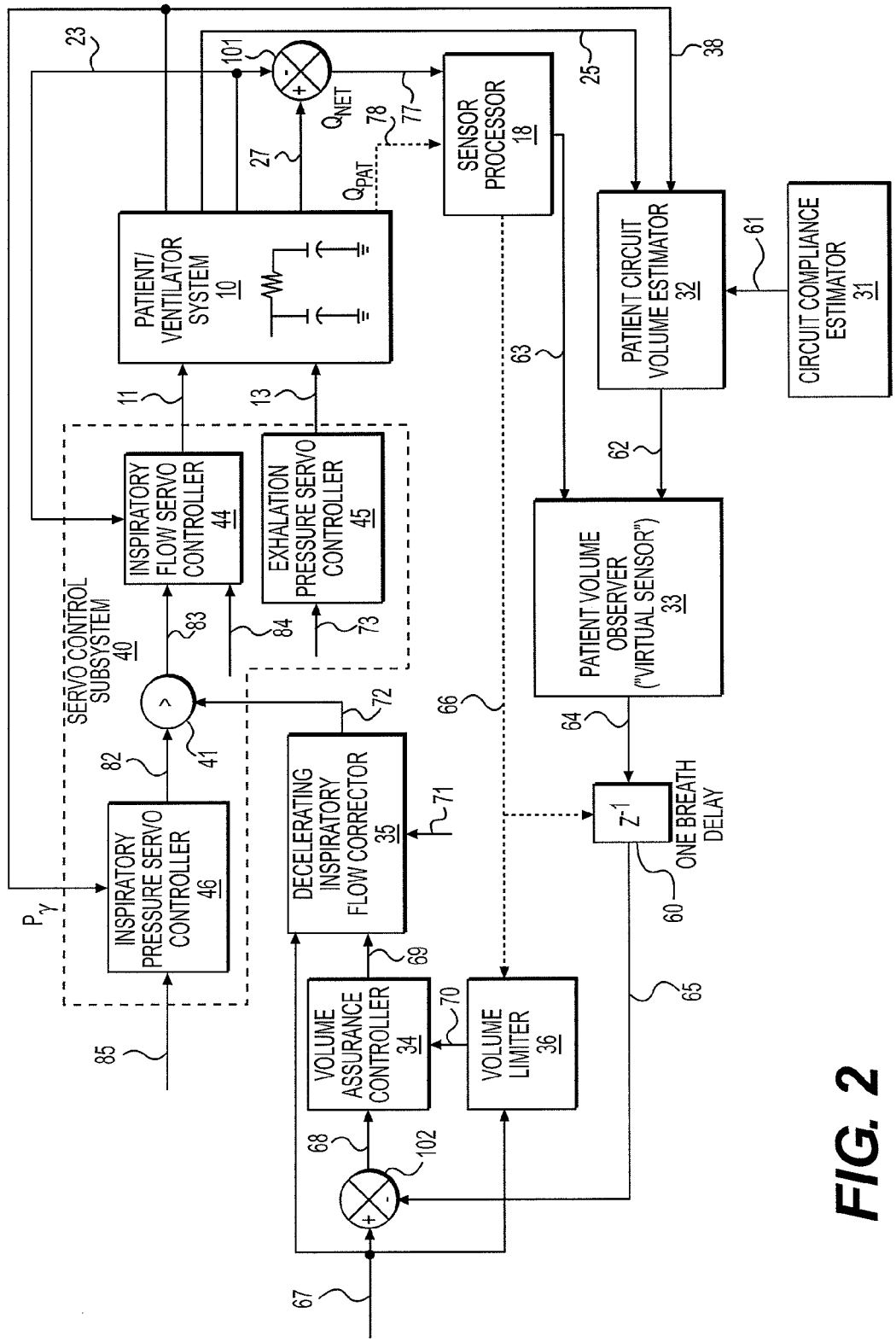
FIG. 2 shows a block diagram of the system for circuit compliance compensated volume assured pressure control and the servo control subsystem as shown in FIG. 1.

Referring to FIG. 2, the system for circuit compliance compensated volume assured pressure control 30 includes a circuit compliance estimator 31, a patient circuit volume estimator 32, a patient volume observer 33, a volume assurance controller 34, and an inspiratory decelerating flow corrector 35. The circuit compliance $C_T$ of the patient circuit 20 can be estimated by measuring the pressure differential $\Delta P_Y$ at various circuit volumes $V_{CC}$. In this embodiment, the circuit compliance estimator 31 is operative to provide a relationship between the circuit volume $V_{CC}$ and the pressure differential $\Delta P_Y$ based on empirical data.

The relationship may be in the form of a mathematical equation of $V_{cc}$ and $\Delta Py$ or a lookup table reflecting the corresponding circuit volumes $V_{cc}$ for a specific circuit pressure $\Delta Py$. When the empirical data shows a linear relationship as expressed by Equation (2) as:

$$V_{CC} = CKT\_CMP_{SLP}(P_y - PEEP) + CKT\_CMP_{INT} \quad (2);$$

where the slope $CKT\_CMP_{SLP}$ and the intercept $CKT\_CMP_{INT}$ 61 are estimated by the circuit compliance estimator 31. The slope $CKT\_CMP_{SLP}$ and the intercept $CKT\_CMP_{INT}$ of the circuit compliance estimator 31 are then output to the patient circuit volume estimator 32. The circuit volume estimator 32 is also connected to the ventilator 10 or the sensor processor 18 for receiving patient pressure $P_y$ and the PEEP, such that the pressure differential $\Delta P_y$ can be computed. Based on $\Delta P_y$, the slope $CKT\_CMP_{SLP}$ and the intercept $CKT\_CMP_{INP}$, the patient circuit volume $V_{cc}$ can be estimated by Equation (2) and denoted as $VOL_{CKT\_EST}$ output 62 to the patient volume observer 33.

The patient volume observer 33 is operative to receive the measured net machine delivered volume $VOL_{NET}$ 63. That is, the machine delivered net volume is derived by integrating the net flow $Q_{NET}$ 77, and the estimated circuit volume $VOL_{CKT\_EST}$ 62 is estimated by the circuit volume estimator 32. By subtracting the estimated circuit volume $VOL_{CKT\_EST}$ 62 from the measured machine delivered net volume $VOL_{NET}$ 63 derived by integrating the net flow $Q_{NET}$ 77, the true tidal volume $VOL_{TID}$ delivered to the patient, that is, the estimated patient volume $VOL_{TID\_EST}$ 64, can be obtained by the patient volume observer (virtual sensor) 33.

When a patient circuit disconnect is detected or when any type of circuit integrity alarm is activated, the volume variables will not be updated until the patient circuit is reconnected or the alarm is deactivated. The volume variables are the measured machine delivered net volume $VOL_{NET}$ 63, the estimated patient volume $VOL_{TID\_EST}$ 64, and the estimated circuit volume $VOL_{CKT\_EST}$ freeze at the previously computed values as:

$$VOL_{NET_K} = VOL_{NET_{K-1}};$$

$$VOL_{CKT\_EST_K} = VOL_{CKT\_EST_{K-1}}; \text{ and}$$

$$VOL_{TID\_EST_K} = VOL_{TID\_EST_{K-1}} \quad (3)$$

where K is an index for indicating the currently computed variables and K-1 for indicating the previously computed variables. The sampling intervals can be variable according to specific conditions, requirements, or setup parameters.

When the y flow sensor 28 is installed at the patient Y piece 26 via y flow sensor line 29 of the patient circuit 20, the patient flow $Q_y$ 9 can be measured, and a measured patient volume $VOL_{TID\_Y}$ 66 can be computed to facilitate volume limit of the volume assurance controller 34 so as to prevent an excessive volume compensation factor $VOL_{TID\_CTL}$ 69 from being generated and output therefrom. The measured patient volume $VOL_{TID\_Y}$ 66 can also be used to replace the estimated patient volume $VOL_{CKT\_EST}$ as a feedback patient volume used to estimate the volume compensation factor $VOL_{TID\_CTL}$ 69 in the volume assurance controller 34. The application of the measured patient volume $VOL_{TID\_Y}$ 66 will be discussed in detail below.

In addition to the measured patient volume $VOL_{TID\_Y}$ 66, another volume variable, the inspiratory volume $VOL_{INSP}$, can also be obtained by integrating the inspiratory flow $Q_{INSP}$ 23. Similar to the volume variables presented in Equation (3), computation of these two volume variables are frozen at the previously computed values whenever patient circuit disconnect is detected or when a circuit integrity alarm is activated. These two volume variables are frozen at the previously computed values as:

$$VOL_{TID\_Y_K} = VOL_{TID\_Y_{K-1}}; \text{ and}$$

$$VOL_{INSP_K} = VOL_{INSP_{K-1}} \quad (3\text{-}1)$$

Preferably, at the start of every inspiratory phase, the measured machine delivered net volume $VOL_{NET}$ 63, the measured patient volume $VOL_{TID\_Y}$ 66, and the inspiratory volume $VOL_{INSP}$ are reset to an initial value (0 in this embodiment) and updated from the initial value every sampling interval (e.g., every 2 msec) as:

$$VOL_{NET_{K-}} = 0, VOL_{NET_K} = (Q_{NET_K}/60)*0.002$$

$$VOL_{TID\_Y_{K-1}} = 0, VOL_{TID\_Y_K} = (Q_{Y_K}/60)*0.002$$

$$VOL_{INSP_{K-1}} = 0, VOL_{INSP_K} = (Q_{INSP_K}/60)*0.0002 \quad (4)$$

During the inspiratory phase, the net flow $Q_{NET}$ 77, the patient delivered flow $Q_y$ 9, and the inspiratory flow $Q_{INSP}$ 23 are continuously monitored. When the inspiratory phase has started for at least a predetermined period of time (such as for 50 milliseconds) and the net flow $Q_{NET}$ 77 is detected to cross zero, that is, when $Q_{NET_K} < 0$ and $Q_{NET_{K-1}} > 0$, a zero-crossing net flow is detected and flagged while the net machine delivered volume $VOL_{NET}$ 63, the measured patient volume $VOL_{TID\_Y}$ 66, and the inspiratory volume $VOL_{INSP}$ are continuously updated as:

$$VOL_{NET_K} = VOL_{NET_{K-1}} + (Q_{NET_K}/60)*0.002,$$
$$VOL_{NET_K} = \max(VOL_{NET_K}, 0)$$

$$VOL_{TID\_Y_K} = VOL_{TID\_Y_{K-1}} + (Q_{Y_K}/60) * 0.002,$$
$$VOL_{TID_K} = \max(VOL_{TID\_Y_K}, 0)$$

$$VOL_{INSP_K} = VOL_{INSP_{K-1}} + (Q_{INSP_K}/60) * 0.002 \quad (5)$$

Upon entering the expiratory phase, if the net flow $Q_{NET}$ 77 has been detected to cross zero during the inspiratory phase, the estimated circuit volume $VOL_{CKT\_EST}$ and the estimated patient volume $VOL_{TID\_EST}$ 64 are updated at the start expiratory phase immediately following the inspiratory phase as:

$$VOL_{CKT\_EST_K} = \quad (6)$$
$$\begin{cases} CKT\_CMP_{SLP} \cdot (P_{Y_K} - PEEP_K) + CKT\_CMP_{INT}, & circuit compliance compensation enabled \\ 0, & circuit compliance compensation disabled \end{cases}$$

10 cm$H_2O$ $$VOL_{CKT\_EST_K} = \max(VOL_{CKT\_EST_K}, 0)$$
$$VOL_{TID\_EST_K} = VOL_{NET_K} - VOL_{CKT\_EST_K}$$
$$VOL_{TID\_EST_K} = \max(VOL_{TID\_EST_K}, 0),$$

and the machine delivered net volume $VOL_{NET}$ 63 and the measured patient volume $VOL_{TID\_Y}$ 66 are reset to the initial setup values and updated from the initial setup values as:

$$VOL_{NET_{K-1}} = 0, VOL_{NET_K} = (Q_{NET_K}/60)*0.002,$$
$$VOL_{NET_K} = \min(VOL_{NET_K}, 0)$$

$$VOL_{TID\_Y_K} = 0, VOL_{TID\_Y_K} = (Q_{Y_K}/60)*0.002,$$
$$VOL_{TID\_Y_K} = \min(VOL_{TID\_Y_K}, 0) \quad (7)$$

If the net flow $Q_{NET}$ 77 does not cross zero during the inspiratory phase, the machine delivered net volume $VOL_{NET}$ 63 and the measured patient volume $VOL_{TID\_Y}$ 66 will not be reset at the start of the expiratory phase. That is, the machine delivered net volume $VOL_{NET}$ 63 and the measured patient volume $VOL_{TID\_Y}$ 66 are continuously updated during the expiratory phase as Equation (5). The inspiratory volume $VOL_{INSP}$ is also continuously updated as equation (5). However, when the zero-crossing net flow $Q_{NET}$ is detected within a predetermined period of time such as 100 msec after the machine breath has cycled to the expiratory phase (that is, when $TIME_{EXP} < 100$ msec, $Q_{NETK} < 0$ and $Q_{NETK-1} > 0$); or alternatively, when the expiratory phase has extended over the predetermined period such as 100 msec before the zero-crossing net flow $Q_{NET}$ is detected (that is, $TIME_{EXP} > 100$ msec and $Q_{NETK} > 0$), the estimated circuit volume $VOL_{CKT\_EST}$ and the estimated patient volume $VOL_{TID\_EST}$ 64 are updated according to Equation (6), while the measured machine delivered net volume $VOL_{NET}$ 63 and the measured patient volume $VOL_{TID\_Y}$ 66 are reset and updated as:

$$VOL_{NETK-1} = 0, VOL_{NETK} = (Q_{NET}/60)*0.002,$$
$$VOL_{NETK} = \min(VOL_{NETK}, 0)$$

$$VOL_{TID\_YK} = 0, VOL_{TID\_YK} = (Q_{TIDK}/60)*0.002,$$
$$VOL_{TID\_YK} = \min(VOL_{TID\_YK}, 0) \quad (8)$$

In this embodiment, the measured machine delivered net volume $VOL_{NET}$ 63 and the measured patient volume $VOL_{TID\_Y}$ 66 are reset according to the timing when the net flow $Q_{NET}$ crosses zero instead of the phase transition of machine breath. This allows the calculations of the estimated circuit volume $VOL_{CKT\_EST}$ and the estimated patient volume $VOL_{TID\_EST}$ 64 to be synchronized with true patient inhalation and exhalation. In this way, a more accurate patient volume can be computed. The estimated patient volume is thus updated according to the timing when the net flow $Q_{NET}$ crosses zero such that the entirety of the machine delivered net volume $VOL_{NET}$ 63 can be accounted for even when the patient breath and the machine breath are out of phase, that is, when the net flow $Q_{NET}$ does not cross zero at the time the machine breath is cycling to the expiratory phase.

Referring now to FIG. 2, at the beginning of every inspiratory phase, the estimated patient volume $VOL_{TID\_EST}$ 64, obtained by the patient volume observer 33, is delayed at one breath delay 60 and is then subtracted from an assured volume $VOL_{ASS\_SET}$ preset 67 by the user by an adder/subtractor 102 as:

$$VOL_{TID\_ERRK} = VOL_{ASS\_SETK} - VOL_{TID\_ESTK-1} \quad (9)$$

The volume differential, namely, the volume error $VOL_{TID\_ERR}$ 68, between the assured volume $VOL_{ASS\_SET}$ and the estimated patient volume $VOL_{TID\_EST}$ 64 indicates the error between the desired and actual amounts of volume delivered to the patient. The volume error $VOL_{TID\_ERR}$ 68 is then used by the volume assurance controller 34 for estimating a volume compensation factor in order to compensate for errors in patient volume delivery.

Figure 3:
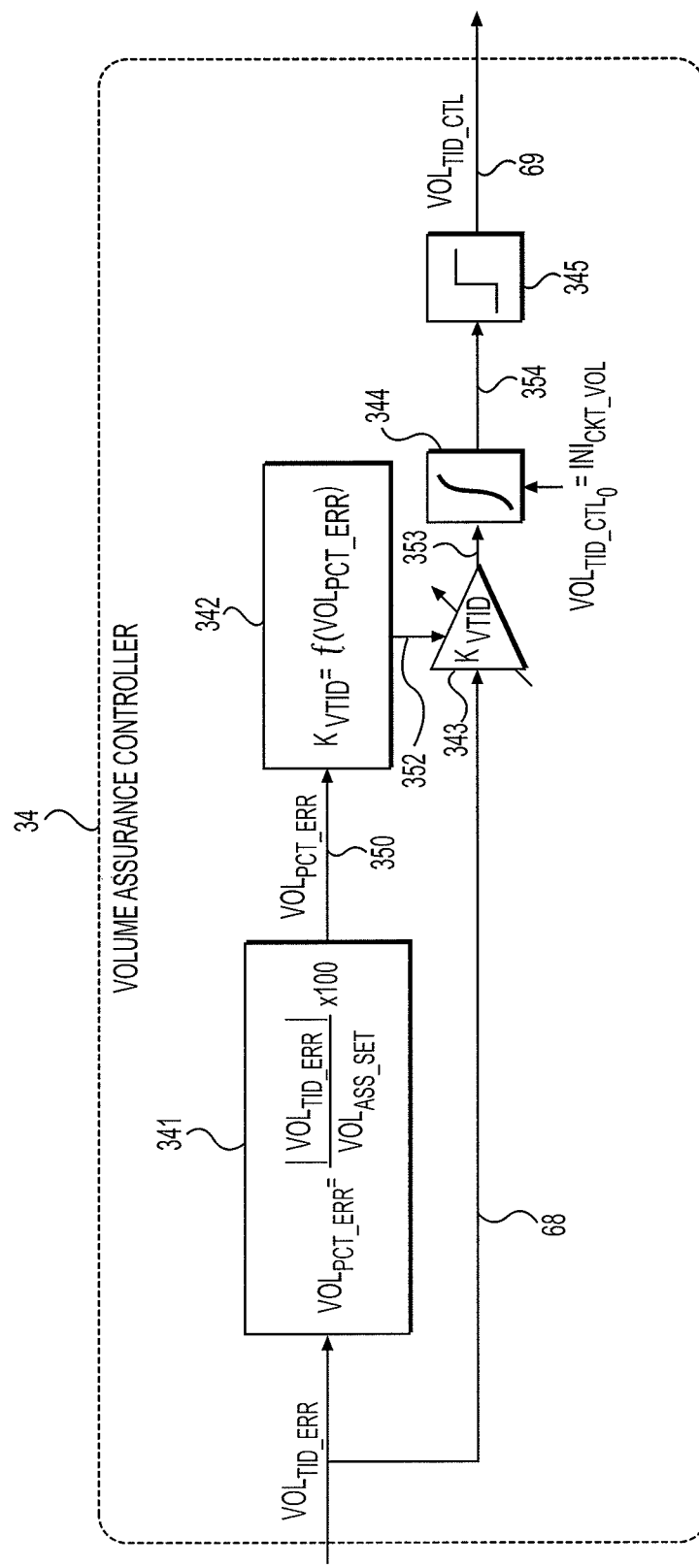
FIG. 3 is a block diagram showing a volume assurance controller of the system for circuit compliance compensation volume assured pressure control.

As shown in FIG. 3, the volume assurance controller 34 further includes error percentage converter 341, a gain scheduler 342, a multiplier 343, an integrator 344, and a volume restrictor 345. Upon receiving the volume error $VOL_{TID\_ERR}$ 68, the error percentage converter 341 converts the volume error $VOL_{TID\_ERR}$ 68 into a volume error percentage $VOL_{PCT\_ERR}$ as:

$$VOL_{PCT\_ERR} = \frac{|VOL_{TID\_ERR}|}{VOL_{ASS\_SET}} \times 100\% \quad (10)$$

The error percentage $VOL_{PCT\_ERRK}$ provides a useful indication of the ratio between the circuit compliance $C_T$ and the lung compliance $C_L$ of the patient. More specifically, when the error percentage $VOL_{PCT\_ERRK}$ is large, it indicates that a majority of the measured machine delivered net volume $VOL_{NET}$ 63 is distributed to the patient circuit 20 instead of being supplied to the patient's lung. Under such circumstance, a larger amount of volume may be required to compensate for the circuit compliance $C_T$ in order to ensure that the desired assured volume $VOL_{ASS\_SET}$ as preset can be delivered to the patient's lungs. Therefore, the gain scheduler 342 is provided to generate a gain $K_{VTID}$ 352 according to the error percentage $VOL_{PCT\_ERR}$ 350 for dynamically weighting the feedback volume error $VOL_{TID\_ERR}$, proportional to the error percentage $VOL_{PCT\_ERR}$. The gain $K_{VTID}$ 352 can be expressed as a function of the volume error $VOL_{TID\_ERR}$ as:

$$K_{VTID} = f(VOL_{TID\_ERR}) \quad (11)$$

The gain $K_{VTID}$ 352 is then provided to the multiplier 343 to factor the volume error $VOL_{TID\_ERR}$, and the weighted volume error $VOL_{TID\_ERR}$353 is then outputted to the integrator 344 from which an updated volume compensation factor $VOL_{TJD\_CTL}$354 can be obtained. More specifically, the product of the gain $K_{VTID}$ 352 and the volume error $VOL_{TID\_ERR}$353, that is, the weighted volume error, is added to the volume compensation factor $VOL_{TID\_CTL}$ 69 computed in the previous breath in the integrator 344. The volume compensation factor, $VOL_{TID\_CTLK}$, for the current breath can be estimated as:

$$VOL_{TID\_CTLK} = K_{VTID} * VOL_{TID\_ERRK} + VOL_{TID\_CTLK\_1} \quad (12)$$

It will be appreciated that, at the start of the ventilation, no updated or computed volume compensation factor $VOL_{TID\_CTL}$69 is available. Therefore, the volume compensation factor $VOL_{TID\_CTL}$69 is initialized as:

$$VOL_{\text{TID\_CTL}_0} = \begin{cases} \text{INI\_CKT\_VOL}, & \text{circuit compliance compensation enabled} \\ 0, & \text{circuit compliance compensation disabled} \end{cases} \quad (13)$$

The volume compensation factor $VOL_{TID\_CTL}$69 is also reset according to Equation (13) whenever any user settings of the ventilator 10 are altered. That is, any time when a new set of parameters is input to the system, the volume compensator factor, $VOL_{TIC\_CTL}$, will be reset according to equation (13) and updated thereafter.

The volume assurance controller 34 further comprises a volume restrictor 345 to prevent a negative circuit compliance volume compensation factor $VOL_{TID\_CTL}$69 from being outputted. That is, the volume restrictor 345 restricts the output of the volume assurance controller 34 between a maximum value and zero as:

$$VOL_{TID\_CTLK} 32 \max.(VOL_{TID\_CTLK}, 0) \quad (14)$$

As discussed above, the measured patient volume $VOL_{TID\_Y}$ 66 can be used as a volume limit to prevent the volume assurance controller 34 from generating an excessive volume compensation factor to compensate for the circuit compliance. To this extent, the system for circuit compliance compensated pressure control 30 further comprises a volume limiter 36 operative to receive the measured patient volume $VOL_{TID\_y}$ 66 and compare the measured patient volume $VOL_{TID\_Y}$ 66 to the preset assured volume $VOL_{ASS\_SET}$. Before the measured patient volume $VOL_{TID\_Y}$ 66 reaches the preset assured volume $VOL_{ASS\_SET}$ and when the estimated patient volume $VOL_{TID\_EST}$ 64 has been updated or the circuit compliance compensation is enabled, that is, when $VOL_{TID\_Y} < VOL_{ASS\_SET}$ and $VOL_{TID\_EST} > 0$, the volume delivery controller 34 operates normally to generate the volume compensation factor $VOL_{TID\_CTL}$ 69 based on Equations (10) to (14).

If the circuit compliance compensation is not enabled and the preset assured volume $VOL_{ASS\_SET}$ is larger than the measured patient volume $VOL_{TID\_Y}$ 66, the output of the volume assurance controller 34 is limited to a percentage of leak compensation $MAX_{PCT\_LKCMP}$ and is computed as:

$$VOL_{TID\_ERRK} = VOL_{ASS\_SETK} - VOL_{TID\_ESTK-1}$$

$$VOL_{TID\_CTLK} = VOL_{TID\_ERRK} + VOL_{TID\_CTLK-1}$$

$$VOL_{TID\_CTLK} = \min(MAX_{PCT\_LKCMP} * VOL_{ASS\_SET}, VOL_{TID\_CTLK})$$

$$VOL_{TID\_CTLK} = \max(-MAX_{PCT\_LKCMP} * VOL_{ASS\_SET}, VOL_{TID\_CTLK}) \quad (15)$$

When the measured patient volume $VOL_{TID\_Y}$ 66 reaches the preset assured volume $VOL_{ASS\_SET}$, the volume error $VOL_{TID\_ERR}$ is zero and the volume compensation factor is frozen at the previously computed one as:

$$VOL_{TID\_ERRK} = 0$$

$$VOL_{TID\_CTLK} = VOL_{TID\_CTLK-1} \quad (16)$$

Further referring to FIG. 2, the volume compensation factor $VOL_{TID\_CTL}$ is output from the volume assurance controller 34 to the decelerating inspiratory flow corrector 35, in which a maximum inspiratory peak flow $Q_{INSP\_PEAK}$ is determined according to the volume compensation factor $VOL_{TID\_CTL}$, the preset assured volume $VOL_{ASS\_SET}$, and a preset inspiratory time $T_{INSP\_SET}$ as:

$$Q_{\text{INSP\_PEAKK}} = \frac{4/3 * (VOL_{\text{ASS\_SET}_K} + VOL_{\text{TID\_CTL}_K}) * 60}{T_{\text{INSP\_SET}_K}} \quad (17)$$

Once the maximum peak inspiratory flow $Q_{INSP\_PEAK}$ is obtained, the inspiratory flow $Q_{INSP\_SET}$72 can be modulated as a function of the inspiratory time and can be computed by:

$$Q_{\text{INSP\_SET}_K} = Q_{\text{INSP\_PEAKK}} - T_{\text{INSPK}} * \left( \frac{Q_{\text{INSP\_PEAK}_K}}{2 * T_{\text{INSP\_SETK}}} \right) \quad (18)$$

Figure 4:
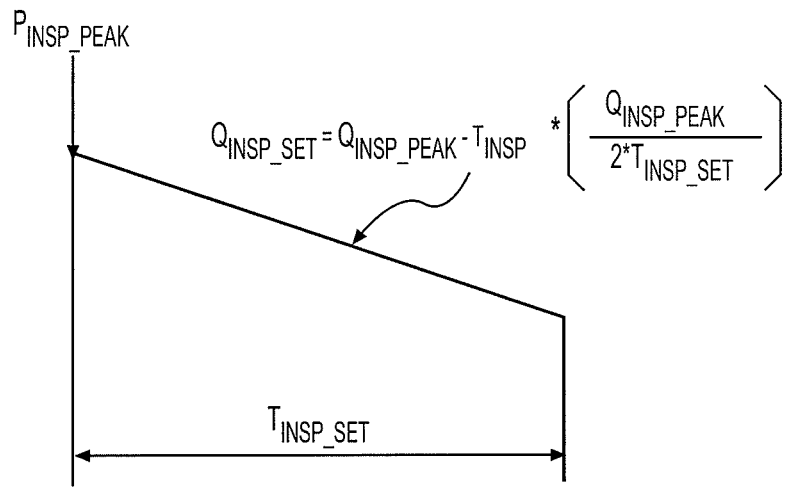
FIG. 4 illustrates the inspiratory gas flow.

FIG. 4 illustrates the waveform of the volume assurance decelerating inspiratory flow $Q_{INSP\_SET}$ 72.

A volume assurance decelerating flow command carrying data regarding the modulated volume assurance decelerating inspiratory flow $Q_{INSP\_SET}$ 72 is then outputted from the decelerating inspiratory flow corrector 35 to the servo control subsystem 40. As shown in FIG. 2, the servo control subsystem 40 includes an inspiratory pressure servo controller 46, a comparator 41, an inspiratory flow servo controller 44 and an exhalation pressure servo controller 45. In a pressure control mode of ventilation, an inspiratory pressure $PRS_{INSP\_SET}$ 85 captured at the beginning of every breath is preselected by the user and inputted to the inspiratory pressure servo controller 46.

As shown, upon receiving the estimated patient pressure $P_y$, defined by Equation (1), the inspiratory pressure servo controller 46 is operative to output an inspiratory pressure controller flow $Q_{INSP\_PRSCTL}$ 82 based on the error between the preset inspiratory pressure $PRS_{INSP\_SET}$85 and the estimated patient pressure $P_y$, to the comparator 41. The comparator 41 is then operative to output a final inspiratory flow $Q_{INSP\_DES}$ 83 from the larger amount between the modulated volume assurance decelerating inspiratory flow $Q_{INSP\_SET}$72 and the inspiratory pressure controller flow $Q_{INSP\_PRSCTL}$ 82 to the inspiratory flow servo controller 44. Meanwhile, a preset maximum allowable inspiratory flow $Q_{INSP\_MAX}$ 84 is also input to the inspiratory flow servo controller 44 to ensure the final inspiratory flow $Q_{INSP\_DES}$ 83 carried by the flow control valve signal $FCV_{D/A}$ 1 is within a safe range as:

$Q_{INSP\_DESK} = \max(Q_{INSP\_PRSCTLK}, Q_{INSP\_SETK})$ $Q_{INSP\_DESK} = \min(Q_{INSP\_DESK}, Q_{INSP\_MAX})$ $PRS_{EXH\_DESK} = $ close exhalation valve     (19)

Figure 5:
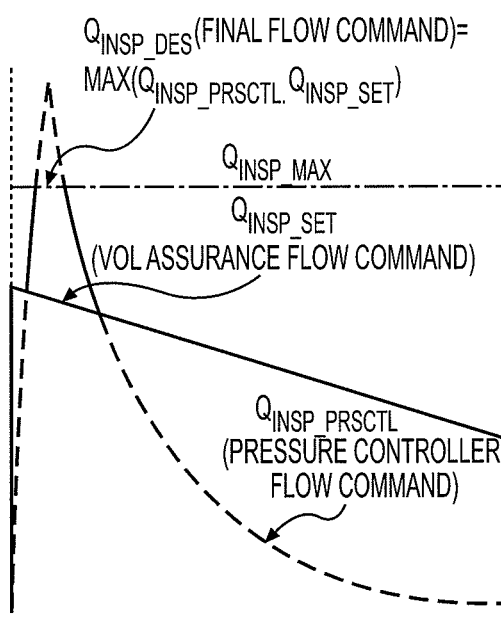
FIG. 5 illustrates the final inspiratory flow command output to be used by the servo control subsystem.

FIG. 5 shows the final inspiratory flow $Q_{INSP\_DES}$ 83 to be used by the inspiratory flow servo controller 44. In addition to the inspiratory flow servo controller 44, as mentioned above, the servo control subsystem 40 further comprises an exhalation pressure servo controller 45 operative to output an exhalation valve control command $EV_{D/A}$ 3 for closing the exhalation valve during inspiration. Its input is $PRS_{EXH\_DES}$ 73. That is, when the inspiratory phase starts, the exhalation valve control command $EV_{D/A}$ 3 is output from the exhalation pressure servo controller 45 to close the exhalation valve of the ventilator 10.

When the inspiratory time $T_{INSP}$ reaches the preset inspiratory time $T_{INSP\_SET}$ 71, and when the inspiratory volume $VOL_{INSP}$ reaches the sum of the preset assured volume $VOL_{ASS\_SET}$ and the volume compensation factor $VOL_{TID\_CTL}$ or when the assured volume $VOL_{ASS\_SET}$ is preset larger than zero and the volume assurance decelerating inspiratory flow $Q_{INSP\_SET}$ 72 is not larger than zero, the breath cycles to the expiratory phase and the exhalation valve is commanded to open.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A circuit compliance compensated volume assured pressure control system, comprising:
   a circuit compliance estimator, operative to estimate a patient circuit compliance;
   a patient circuit volume estimator, operative to estimate a circuit volume $VOL_{CKT\_EST}$ based on the patient circuit compliance and a patient estimated pressure $P_y$;
   a patient volume observer, operative to estimate a patient volume $VOL_{TID\_EST}$ based on a measure delivered net volume $VOL_{NET}$ and the patient circuit compliance;
   a volume assurance controller, operative to generate a circuit compliance volume compensation factor $VOL_{TID\_CTL}$ based on a preset assured volume $VOL_{ASS\_SET}$ and the estimated patient volume $VOL_{TID\_EST}$, and
   a decelerating inspiratory flow corrector, operative to generate a decelerating inspiratory flow command based on a preset inspiratory time $T_{INSP}$, the volume compensation factor $VOL_{TID\_CTL}$ and a preset assured volume $VOL_{ASS\_SET}$.

2. The system of claim 1, further comprising:
   a sensor processor operative to generate and to output the machine delivered net volume $VOL_{NET}$;
   a netflow $Q_{NET}$ integrator operative to integrate a net flow $Q_{NET}$ value defined as by finding a difference between a measured inspiratory flow $Q_{INSP}$ and a measured expiratory flow $Q_{EXP}$.

3. The system of claim 2, wherein said machine delivered net volume $VOL_{NET}$ is updated and reset at the start of the every inspiratory phase.

4. The system of claim 2, wherein:
   the estimated circuit volume $VOL_{CKT\_EST}$, and the estimated patient volume $VOL_{TID\_EST}$ are updated; and
   the measured machine delivered net volume $VOL_{NET}$ is reset at the start of an expiratory phase following an inspiratory phase during which a net flow $Q_{NET}$ crosses zero;
   wherein the system further comprises:
   a netflow $Q_{NET}$ zero crossing detector operative to detect a zero-crossing; and
   a $Q_{NET}$ finder operative to find $Q_{NET}$ by taking a difference between a measured inspiratory flow $Q_{INSP}$ and a measured expiratory flow $Q_{EXP}$ after said zero-crossing has been detected.

5. The system of claim 4, wherein when the net flow $Q_{NET}$ does not cross zero during the inspiratory phase,
   the estimated circuit and patient volumes $VOL_{CKT\_EST}$ and $VOL_{TID\_EST}$ are updated; and
   the measured machine delivered net volume $VOL_{NET}$ is reset when the net flow $Q_{NET}$ crosses zero after the expiratory phase starts or when the expiratory phase has started over a predetermined period of time before the net flow $Q_{NET}$ zero-crossing is detected.

6. The system of claim 1, wherein the volume assurance controller further comprises a gain scheduler:
   wherein the assurance controller is operative to
   generate a dynamic gain $K_{VTID}$ for weighting a volume error $VOL_{TID\_ERR}$ between the preset assured volume $VOL_{ASS\_SET}$ and the estimated patient volume $VOL_{TID\_EST}$; and
   add the volume compensation factor $VOL_{TID\_CTL}$ to the weighted volume error KVTID multiplied with the VOL TID ERR after each breath.

7. The system of claim 6, wherein the volume assurance controller further comprises a volume error percentage converter for converting the volume error $VOL_{TID\_ERR}$ into an error percentage $$VOL_{PCT\_ERR} \text{ by } VOL_{PCT\_ERR} = \frac{|VOL_{TID\_ERR}|}{VOL_{ASS\_SET}} \times 100\%,$$

so as to compute the dynamic gain $K_{VTID}$ as a function thereof.

8. The system of claim 7, wherein the volume assurance controller further comprises:
   a multiplier for multiplying the dynamic gain $K_{VTID}$ with the preset assured volume $VOL_{ASS\_SET}$.

9. The system of claim 8, wherein the volume assurance controller further comprises an integrator operative to provide the volume compensation factor for a current breath by adding an output of the product of $K_{VTID}$ and $VOL_{ASS\_SET}$ with the volume compensation factor $VOL_{TID\_CTL}$ obtained from a previous breath.

10. The system of claim 9, wherein the integrator is operative to receive an initialized value $INI_{CKT\_VOL}$ of the volume compensation factor $VOL_{TID\_CTL}$ for a first breath of ventilation.

11. The system of claim 6 wherein the volume assurance controller further comprises a volume restrictor operative to prevent the volume compensation factor $VOL_{TID\_CTL}$ exceeding a safety range from being output.

12. The system of claim 1, further comprising a volume limiter operative to limit the volume compensation factor $VOL_{TID\_CTL}$ output from the volume assurance controller according to a patient volume $VOL_{TID\_Y}$ measured from a Y flow sensor.

13. The system of claim 12, wherein before the measured patient volume $VOL_{TID\_Y}$ reaches the preset assured volume $VOL_{ASS\_SET}$ and the circuit compliance compensation is disabled, the volume limiter is operative to control the volume assurance controller to output the volume compensation factor using:
   a) a volume error computer operative for computing a volume error $VOL_{TID\_ERR}$ by a difference between the assured volume $VOL_{ASS\_SET}$ preset for a current breath and the patient volume $VOL_{TID\_EST}$ estimated from a previous breath;
   b) a volume compensation factor computer operative for computing the volume compensation factor of the current breath by adding the volume error $VOL_{TID\_ERR}$ to the volume compensator factor obtained from the previous breath; and
   c) a volume compensation factor limiter operative for limiting the volume compensation factor of the current breath between a maximum and minimum value.

14. The system of claim 13, wherein when the measured patient volume $vol_{TID\_Y}$ reaches the preset assured volume $VOL_{ASS\ SET}$, the volume assurance controller is operative to output the volume compensation factor $VOL_{TID\_CTL}$ obtained from the previous breath.

15. The system of claim 1, wherein the decelerating inspiratory flow corrector is operative to compute a maximum inspiratory peak flow $Q_{INSP\_PEAK}$ by:

$$Q_{\text{INSP\_PEAK}} = \frac{4/3*(VOL_{\text{ASS\_SETk}} + VOL_{\text{TID\_CTLk}})*60}{T_{\text{INSP\_SETk}}}.$$

16. The system of claim 15, wherein the decelerating inspiratory flow corrector is operative to compute a modulated decelerating inspiratory flow $Q_{INSP\_SET}$ by:

$$Q_{\text{INSP\_SET}} = Q_{\text{INSP\_PEAK}} - T_{INSPk} * \frac{Q_{\text{INSP\_PEAK}}}{2*T_{\text{INSP\_SETk}}}.$$

17. A system for circuit compliance compensated volume assured pressure control in a patient ventilation circuit, comprising:
   a volume assurance controller operative to provide an estimated circuit compliance volume compensation factor $VOL_{TID\_CTL}$ based on a patient estimated pressure $P_y$, an estimated or measured patient volume, $VOL_{TID\_EST}$ or $VOL_{TID\_Y}$, and a preset assured volume $VOL_{ASS\_SET}$; and
   a decelerating inspiratory flow corrector operative to modulate an inspiratory flow $Q_{INSP\_SET}$ based on a preset waveform, a preset inspiratory time $T_{INSP\_SET}$, a preset assured volume $VOL_{ASS\_SET}$ and the volume compensation factor $VOL_{TID\_CTL}$ output from the volume assurance controller.

18. The system of claim 17, further comprising a patient volume observer operative to provide the estimated patient volume $VOL_{TID\_EST}$ from a measured machine delivered net volume $VOL_{NET}$.

19. The system of claim 18, wherein the measured machine delivered net volume $VOL_{NET}$ integrated from a net flow $Q_{NET}$ defined as a flow difference between a measure inspiratory flow $Q_{INSP}$ and a measured expiratory flow $Q_{EXP}$.

20. The system of claim 18, further comprising a circuit volume estimator operative to provide an estimated circuit volume $VOL_{CKT\_EST}$ according to an estimated circuit compliance.

21. The system of claim 20, wherein the patient volume estimator is operative to subtract the estimated circuit volume $VOL_{CKT\_EST}$ from the measured machine delivered net volume $VOL_{NET}$ as the estimated patient volume $VOL_{TID\_EST}$ and output the estimated patient volume $VOL_{TID\_EST}$ to the volume assurance controller.

22. The system of claim 17, further comprising:
   a patient flow sensor operative to provide the measured patient volume $VOL_{TID\_Y}$; and
   a measured patient volume integrator operative to integrate the measured patient volume producing a patient flow $Q_y$.

23. The system of claim 17, wherein the volume assurance controller further comprises a gain scheduler operative to provide a weighting gain $K_{VTID}$ as a function of a volume percentage $VOL_{PCT\_ERR}$, —wherein the volume percentage $VOL_{PCT\_ERR}$ is defined as an absolute value of a volume error $VOL_{TID\_EST}$ between a preset assured volume $VOL_{ASS\_SET}$ and the estimated or measured patient volume $VOL_{TID\_EST}$ or $VOL_{TID\_Y}$ divided by the preset assured volume $VOL_{ASS\_SET}$.

24. The system of claim 23, wherein the volume compensation factor $VOL_{TID\_CTL}$ is initialized with an initial value $INI_{CKT\_VOL}$ at a first breath of ventilation provided by the patient ventilation circuit.

25. The system of claim 24, wherein the volume assurance controller further comprises a multiplier for multiplying the weighting gain $K_{VTID}$ with the volume error $VOL_{TID\_ERR}$.

26. The system of claim 25, wherein the volume assurance controller further comprises an integrator operative to add an output of the multiplier with the volume compensation factor $VOL_{TID\_CTL}$ obtained from a previous breath.

27. The system of claim 17, wherein the decelerating inspiratory flow corrector is operative to compute a maximum peak inspiratory flow $Q_{INSP\_PEAK}$ by:

$$Q_{\text{INSP\_PEAK}} = \frac{4/3*(VOL_{\text{ASS\_SETk}} + VOL_{\text{TID\_CTLk}})*60}{T_{\text{INSP\_SETk}}}.$$

28. The system of claim 27, wherein the decelerating inspiratory flow corrector is operative to compute a modulated decelerating inspiratory flow $Q_{INSP\_SET}$ by:

$$Q_{\text{INSP\_SETk}} = Q_{\text{INSP\_PEAKk}} - T_{INSPk} * \frac{Q_{\text{INSP\_PEAKk}}}{2*T_{\text{INSP\_SETk}}}$$

29. A patient respiratory ventilation circuit, comprising:
   a ventilator, operative to provide an inspiratory gas to and receive an expiratory gas from a patient via a patient circuit;
   a system for circuit compliance compensated volume assured pressure control, comprising:
   a volume assurance controller operative to provide an estimated circuit compliance volume compensation factor $VOL_{TID\_CTL}$ based on an estimated or measured patient volume, $VOL_{TID\_EST}$ or $VOL_{TID\_Y}$, and a preset assured volume $VOL_{ASS\_SET}$; and
   a decelerating inspiratory flow corrector operative to modulate an inspiratory flow $Q_{INSP\_SET}$ based on a preset waveform, a preset inspiratory time $T_{INSP\_SET}$, a preset assured volume $VOL_{ASS\_SET}$, and the volume compensation factor $VOL_{TID\_CTL}$ output from the volume assurance controller; and a servo control subsystem operative to control a flow control valve and an exhalation valve of the ventilator according to the preset waveform, the preset inspiratory time $T_{INSP\_SET}$, and the larger amount between the inspiratory flow $Q_{INSP\_SET}$ modulated by the decelerating inspiratory flow corrector and an inspiratory pressure controller flow $Q_{INSP\_PRSCTL}$.

30. The circuit of claim 29, wherein the volume assured pressure control system further comprises a patient volume observer operative to provide the estimated patient volume $VOL_{TID\_EST}$ from a measured machine delivered net volume $VOL_{NET}$.

31. The circuit of claim 30, wherein the measured machine delivered net volume $VOL_{NET}$ is integrated from a net flow $Q_{NET}$ defined as a flow difference between a measure inspiratory flow $Q_{INSP}$ and a measured expiratory flow $Q_{EXP}$.

32. The circuit of claim 31, wherein the volume assured pressure control system further comprises a circuit volume estimator operative to provide an estimated circuit volume $VOL_{CKT\_EST}$ according to an estimated circuit compliance.

33. The circuit of claim 32, wherein the patient volume estimator is operative to subtract the estimated circuit volume $VOL_{CKT\_EST}$ from the measured machine delivered net volume $VOL_{NET}$ as the estimated patient volume $VOL_{TID\_EST}$ and output the estimated patient volume $VOL_{TID\_EST}$ to the volume assurance controller.

34. The circuit of claim 29, wherein the volume assured pressure control system further comprises a patient flow sensor operative to provide the measured patient volume $VOL_{TID\_Y}$ by integrating a patient flow $Q_y$ measured thereby.

35. The circuit of claim 29, wherein the volume assurance controller further comprises a gain scheduler operative to provide a weighting gain $K_{VTID}$ as a function of a volume percentage $VOL_{PCT\_ERR}$, wherein the volume percentage $VOL_{PCT\_ERR}$ is defined as an absolute value of a volume error $VOL_{TID\_ERR}$ between a preset assured volume $VOL_{ASS\_SET}$ and the estimated or measured patient volume $VOL_{TID\_EST}$ or $VOL_{TID\_Y}$ divided by the preset assured volume $VOL_{ASS\_SET}$.

36. The circuit of claim 35, wherein the volume compensation factor $VOL_{TID\_CTL}$ is initialized with an initial value $INI_{CKT\_VOL}$ at a first breath of ventilation provided by the patient ventilation circuit.

37. The circuit of claim 36, wherein the volume assurance controller further comprises a multiplier for multiplying the weighting gain $K_{VTID}$ with the volume error $VOL_{TID\_ERR}$.

38. The circuit of claim 37, wherein the volume assurance controller further comprises an integrator operative to add an output of the multiplier with the volume compensation factor $VOL_{TID\_CTL}$ obtained from a previous breath.

39. The circuit of claim 29, wherein the decelerating inspiratory flow corrector is operative to compute a maximum peak inspiratory flow $Q_{INSP\_PEAK}$ by:

$$Q_{\text{INSP\_PEAKK}} = \frac{4/3 * (VOL_{\text{ASS\_SETk}} + VOL_{\text{TID\_CTLk}}) * 60}{T_{\text{INSP\_SETk}}}$$

40. The circuit of claim 29, wherein the decelerating inspiratory flow corrector is operative to compute an a modulated decelerating inspiratory flow $Q_{INSP\_SET}$ by:

$$Q_{\text{INSP\_SETk}} = Q_{\text{INSP\_PEAKk}} - T_{INSPk} * \left( \frac{Q_{\text{INSP\_PEAKk}}}{2 * T_{\text{INSP\_SETk}}} \right).$$

41. The circuit of claim 29, wherein the servo control subsystem further comprises:
an inspiratory pressure servo controller operative to output an inspiratory pressure controller flow $Q_{INSP\_PRSCTL}$ computed based on an error between a preset inspiratory pressure $PRS_{INSP\_SET}$ captured at the beginning of every breath and a measured patient pressure $P_y$,
a comparator operative to output a final inspiratory flow $Q_{INSP\_DES}$ from the larger amount between the modulated decelerating inspiratory flow $Q_{INSP\_SET}$ and the inspiratory pressure controller flow $Q_{INSP\_PRSCTL}$;
an inspiratory flow servo controller operative to receive the final inspiratory flow $Q_{INSP\_DES}$ and a preset maximum allowable inspiratory flow $Q_{INSP\_MAX}$ to generate a flow control valve signal FCVDIA according to the final inspiratory flow $Q_{INSP\_DES}$ restricted under the preset maximum allowable inspiratory flow $Q_{INSP\_MAX}$; and
an exhalation pressure servo controller operative to open or close the exhalation valve of the ventilator.

42. The circuit of claim 41, wherein the exhalation pressure servo controller is operative to open or close the exhalation valve according to an exhalation valve pressure command $PRS_{EXH\_DES}$.

43. The method of claim 42, further comprising:
d) initializing the circuit compliance pressure compensation factor $VOL_{TID\_CTL}$ to the initial value $INI_{CKT\_VOL}$ when any user setup parameter of the ventilation system is changed.

44. The method of claim 43, wherein when the estimated patient volume $VOL_{TID\_EST}$ is selected for generating the volume compensation factor $VOL_{TID\_CTL}$, step (a) further comprises:
a1) providing a machine delivered net flow $Q_{NET}$ by computing a flow differential of a measured inspiratory flow $Q_{IWSP}$ and a measured expiratory flows $Q_{EXP}$; and
a2) integrating the machine delivery net flow $Q_{NET}$ into the machine delivered net volume $VOL_{NET}$.

45. The method of claim 44, wherein when the net flow $Q_{NET}$ is detected to cross zero during an inspiratory phase, at the start of an expiratory phase following the inspiratory phase, the estimated circuit volume $VOL_{CKT\_EST}$ and the estimated patient volume $VOL_{TID\_EST}$ are updated, and the measured machine delivered net volume $VOL_{NET}$ is reset.

46. A method for circuit compliance compensated volume assurance pressure control in a patient respiratory ventilation system, comprising:
a) measuring a patient volume $VOL_{TID\_Y}$ through a flow sensor installed at a patient piece of a patient circuit in the ventilation system, or estimating a patient volume $VOL_{TID\_EST}$ based on a machine delivered net volume $VOL_{NET}$ and a circuit compliance CT of the patient circuit; and
b) predetermining an initial value $INI_{CKT\_VOL}$ for a circuit compliance volume compensation factor $VOL_{TID\_CTL}$ and updating the volume compensation factor $VOL_{TID\_CTL}$ based on a preset assured volume $VOL_{ASS\_SET}$ and the patient volume $VOL_{TID\_Y}$ or $VOL_{TID\_EST}$ for each breath; and
c) generating an inspiratory flow $Q_{INSP\_SET}$ according to a predetermined waveform, a preset inspiratory time $T_{INSP}$, a preset assured volume $VOL_{ASS\_SET}$, and the volume compensation factor $VOL_{TID\_CTL}$.

47. The method of claim 46, further comprising a step of resetting and updating the measured patient volume $VOL_{TID\_Y}$ and/or the measured machine delivered net volume $VOL_{NET}$ at the beginning of every inspiratory phase.

48. The method of claim 47, wherein step (a) further comprising:
- a3) deriving a relationship between circuit pressure $P_y$ and circuit volume $V_{cc}$ from the circuit compliance $C_T$;
- a4) estimating a circuit volume $VOL_{CKT\_EST}$ from the relationship by providing a measured patient circuit $P_y$; and
- a5) subtracting the estimated circuit volume $VOL_{CKT\_EST}$ from the measured machine delivered net volume $VOL_{NET}$ to obtain the estimated patient volume $VOL_{TID\_EST}$.

49. The method of claim 48, wherein when the net flow $Q_{NET}$ does not cross zero during an inspiratory phase, the estimated circuit volume $VOL_{CKT\_EST}$ and the estimated patient volume $VOL_{TID\_EST}$ are updated, and the measured machine delivered net volume $VOL_{NET}$ is reset at the earlier when the net flow $Q_{NET}$ crosses zero after the expiratory phase starts or when the expiratory phase has started over a predetermined period of time before the net flow $Q_{NET}$ has crossed zero.

50. The method of claim 49, wherein step (b2) further comprising multiplying the gain $K_{VTID}$ with the volume error $VOL_{TID\_ERR}$ to obtain the volume correction.

51. The method of claim 50, wherein step (b) further comprising:
- b4) limiting the updated circuit compliance volume compensation factor between a predetermined allowable range.

52. The method of claim 46, wherein step (b) further comprises:
- b1) computing a volume error percentage $VOL_{PCT\_ERR}$ defined as a ratio of an absolute value of a volume error $VOL_{TID\_ERR}$ to a preset assured volume $VOL_{ASS\_SET}$, wherein the volume error $VOL_{TID\_ERR}$ is a volume differential between the preset assured volume $VOL_{ASS\_SET}$ and the patient volume $VOL_{TID\_Y}$ or $VOL_{TID\_EST}$;
- b2) determining a gain $K_{VTID}$ as a function of the volume error percentage $VOL_{PCT\_ERR}$, so as convert the volume error $VOL_{TID\,ERR}$ into a volume correction for the circuit compliance volume compensation factor $VOL_{TID\_CTL}$; and
- b3) updating the circuit compliance volume compensation factor $VOL_{TID\_CTL}$ by adding the volume correction thereto.

53. The method of claim 46, wherein step (c) further comprises:
- c1) computing a maximum peak flow $Q_{INSP\ PEAK}$ by:

$$Q_{\text{INSP\_PEAKk}} = \frac{4/3 * (VOL_{\text{ASS\_SETk}} + VOL_{\text{TID\_CTLk}}) * 60}{T_{\text{INSP\_SETk}}}; \text{ and}$$

- c2) computing a modulated decelerating inspiratory flow by:

$$Q_{\text{INSP\_SETk}} = Q_{\text{INSP\_PEAKk}} - T_{\text{INSPk}} * \frac{Q_{\text{INSP\_PEAKk}}}{2 * T_{\text{INSP\_SETk}}}$$

54. The method of claim 46, further comprising:
- d1) capturing a preset inspiratory pressure $PRS_{INSP\_SET}$ at the beginning of every breath;
- d2) generating an inspiratory pressure controller flow $Q_{INSP\_PRSCTL}$ based on an error between the preset inspiratory pressure $PRS_{INSP\_SET}$ and a measured patient pressure $P_y$;
- d3) selecting a larger amount between the inspiratory pressure controller flow $QINSP_{PRSCTL}$ and the modulated decelerating inspiratory flow $Q_{INSP\_SET}$ to determine a flow control valve command $FCV_{DIA}$.

55. The method of claim 54, further comprising a step of generating an exhalation valve command to control open/close status of an exhalation valve.

56. The method of claim 55, further comprising a step of closing the exhalation valve during an inspiratory phase.

\* \* \* \* \*